United States Patent [19]

Faryniarz et al.

[11] Patent Number: 5,486,305
[45] Date of Patent: Jan. 23, 1996

[54] NAIL POLISH REMOVER

[75] Inventors: Joseph R. Faryniarz, Oxford; Philip E. Miner, Newtown, both of Conn.

[73] Assignee: Chesebrough-Pond's USA Co., Greenwich, Conn.

[21] Appl. No.: 308,233

[22] Filed: Sep. 19, 1994

[51] Int. Cl.$^6$ .................... C09D 9/00; C11D 7/50
[52] U.S. Cl. ............. 252/162; 252/170; 252/174.19; 252/364; 252/DIG. 8; 424/61; 106/311; 134/38
[58] Field of Search ................ 424/61; 106/311; 134/38; 252/162, 170, 174.19, 364, DIG. 8

[56] References Cited

U.S. PATENT DOCUMENTS

| | | | |
|---|---|---|---|
| 2,211,129 | 8/1940 | Klinkenstein | 252/170 |
| 2,268,642 | 1/1942 | Carter | 252/122 |
| 4,197,212 | 4/1980 | Minton et al. | 252/164 |
| 4,594,111 | 6/1986 | Coonan | 134/3 |
| 4,735,798 | 4/1988 | Bernstein | 424/61 |
| 4,801,331 | 1/1989 | Murase | 106/5 |
| 4,824,662 | 4/1989 | Hofmann | 424/61 |
| 4,867,800 | 9/1989 | Dishart et al. | 134/40 |
| 5,007,969 | 4/1991 | Doscher | 134/38 |
| 5,098,594 | 3/1992 | Doscher | 252/162 |
| 5,204,026 | 4/1993 | Doscher-Good | 252/542 |
| 5,342,536 | 8/1994 | Miner et al. | 252/162 |
| 5,360,580 | 11/1994 | Dotolo et al. | 252/542 |

FOREIGN PATENT DOCUMENTS

| | | |
|---|---|---|
| 0009691 | 4/1980 | European Pat. Off. . |
| 1160908 | 6/1989 | Japan . |

OTHER PUBLICATIONS

Estasol Brochure–1994 Cosmetics & Toiletries, vol. 109, Apr. 1994, p. 15.

*Primary Examiner*—Paul Lieberman
*Assistant Examiner*—Wyatt B. Pratt
*Attorney, Agent, or Firm*—Milton L. Honig

[57] ABSTRACT

A polish-lacquer remover is provided that includes a volatile organic solvent, a $C_4$–$C_{30}$ diester and water. Preferably, the combination further includes an alkylene carbonate. The compositions achieve low volatile organic chemical emissions, excellent lacquer removal and exhibit improved conditioning for cuticles and nails.

9 Claims, No Drawings

NAIL POLISH REMOVER

BACKGROUND OF THE INVENTION

1. Field of the Invention

The invention relates to nail polish removers of low volatile organic chemical content that meet legislated environmental rules and that also have improved lacquer removal efficacy and conditioning properties.

2. The Related Art

Products have long been marketed for the removal of nail polish (lacquer) from fingernails and toenails. These products essentially contain only a solvent (with which to dissolve the lacquer). Typically the solvent will be a relatively volatile material such as acetone or ethyl acetate.

Environmental concerns regarding air pollution, ozone layer destruction and global warming have lead to government regulations requiring reduction of volatile organic components (VOC) in many products including nail polish removers. Substitution of highly volatile solvents by fluids of lower vapor pressure most often results in products having decreased lacquer removing efficacy and consumer aesthetics. For instance water, the least expensive yet relatively high boiling solvent, is quite poor at dissolving hydrophobic polymeric films.

A considerable body of literature is available describing replacement of straight acetone or ethyl acetate removers. For instance, U.S. Pat. No. 2,268,642 (Carter) reports use of a vanishing cream for dissolving nitrocellulose based nail polish. The formula includes major amounts of water and acetone with lesser levels of butyl acetate, butyl alcohol, carbitol and cetyl alcohol.

EP 0 009 691 (Mullin et al.) describes a remover held within a foam structure. Active fluids listed include glycerin, water, ethanol, acetone and ethyl acetate.

U.S. Pat. No. 4,594,111 (Coonan) discloses a liquid phase cleaner-solvent with 50–90% water, 1–15% isopropyl alcohol and 5–40% propylene carbonate.

U.S. Pat. No. 4,735,798 (Bernstein) emphasizes the undesirable effects of drying out fingernails with high acetone systems. Suggested therein is a replacement combination of 30–60% acetone, 10–35% ethyl acetate, 5–20% ethyl alcohol, 5–20% water and 3–15% glycerin. The combination is reported to be a disinfectant and nail strengthener while serving to render subsequent nail polish coatings more adherent.

U.S. Pat. No. 5,007,969 (Doscher) reports a liquid solvent exhibiting low toxicity and superior cleaning ability. This is achieved through a mixture of ethylene or propylene carbonate in combination with an alkyl diether or diester such as ethylene diacetate.

Japanese Patent 1160908 describes a liquid remover system comprising 5–70% acetone, 5–50% water, 5–50% propylene carbonate, 0.5–30% liquid oil and 0.5–30% hydrocarbon. The combination is reported to have low volatility while not harming the nails or skin.

As evidenced from the aforedescribed literature selection, many solvent combinations have shown efficacy. Nonetheless, there is need for still better remover systems.

Accordingly, it is an object of the present invention to provide a nail polish remover that meets or exceeds government regulations on volatile organic chemical emission standards.

Another object of the present invention is to provide a nail polish remover that has improved lacquer removal efficacy.

Still another object of the present invention is to provide a nail polish remover of improved conditioning for cuticles and nails.

These and other objects of the present invention will become more readily apparent through the detailed description of the invention that follows hereinafter.

SUMMARY OF THE INVENTION

A polish-lacquer removing composition is provided that includes:

(i) a volatile organic solvent having 2 to 10 carbon atoms and exhibiting a vapor pressure of more than 0.1 mm at 20° C.;

(ii) a $C_4$–$C_{30}$ diester exhibiting a vapor pressure of less than 0.1 mm at 20° C.; and (iii) an amount of water such that the diester and water are present in a respective weight ratio ranging from about 30:1 to about 1:30, and the combined solvent and water relative to the diester are in a respective weight ratio of about 100:1 to about 6:1.

DETAILED DESCRIPTION OF THE INVENTION

Now it has been found that certain types of esters in combination with water and traditional volatile organic solvents provide improved performance properties. The solvent system of the present invention achieves reduction of VOC while simultaneously improving lacquer removal efficiency and also conditioning nail and cuticle areas.

Accordingly, a first essential element of compositions according to the present invention is that of a volatile organic solvent having from 2 to 10 carbon atoms with a vapor pressure of more than 0.1 mm, preferably of more than 0.5 mm at 20° C. Acetone and ethyl acetate are the volatile solvents of choice. These may, however, be utilized in combination with other solvents such as methyl ethyl ketone. Amount of the solvent will range from about 50 to about 85% by weight of the total composition. Preferably, the amount will range from about 60 to about 80%, optimally from about 70 to about 75% by weight.

A second essential element of compositions according to the present invention is that of a $C_4$–$C_{30}$ diester having a vapor pressure of less than 0.1 mm at 20° C. Most preferred is a diester of the structure:

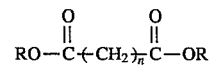

wherein R is a radical selected from the group consisting of $C_1$–$C_6$ alkyl and phenyl radicals; and n is an integer from 1 to 10.

The preferred diester will have R being methyl, ethyl or propyl while n ranges from 1 to 4. Illustrative diesters are the methyl and ethyl esters of succinic, glutaric and adipic acids. Especially preferred is a mixture of 15–20% dimethyl succinate/55–65% dimethyl glutarate/12–23% dimethyl adipate available commercially as Estasol DBE, from the Aceto Corporation, N.Y. Amounts of the diester may range from about 1 to about 30%, preferably from about 3 to about 20%, optimally from about 5 to about 15% by weight.

A third essential element of compositions according to the present invention is water. Amounts of water may range from about 1 to about 30%, preferably from about 5 to about 20%, optimally from about 8 to about 15% by weight.

In relative weight ratio terms, the amount of diester to water may range from about 30:1 to about 1:30, preferably from about 20:1 to 1:20, more preferably from about 10:1 to about 1:10, optimally from about 10:1 to about 1:5 by weight. The weight ratio of total volatile solvent and water relative to diester will range from about 100:1 to about 6:1, preferably from about 20:1 to about 10:1, optimally from about 16:1 to about 12:1.

Advantageously, compositions of the present invention will also include a $C_2-C_4$ alkylene carbonate such as ethylene carbonate or propylene carbonate. Amounts of the alkylene carbonate may range from about 1 to about 30%, preferably from about 3 to about 20%, optimally from about 5 to about 10% by weight. The relative weight ratio of alkylene carbonate to diester will range from about 5:1 to about 1:5, preferably from about 2:1 to about 1:2, optimally about 1:1.

Optional further components of compositions according to the present invention can include humectants such as glycerin, propylene glycol, sorbitol and dimethyl isosorbide. Amounts of these components may range from about 0.1 to about 20% by weight of the total composition.

Emollients such as fatty acid esters, mineral oil, silicone oil, lanolin and lanolin derivatives may also be present in amounts from about 0.01 to about 10% by weight of the total composition. Conditioning agents can be incorporated into the compositions, an example of which is a hydrolyzed protein.

The following example will more fully illustrate selected embodiments of this invention. All parts, percentages and proportions referred to herein and in the appended claims are by weight of the total composition unless otherwise stated.

EXAMPLE 1

An in vitro technique was utilized to evaluate the effectiveness of nail polish removers. The technique employed a Schwan-Stabilo Payoff Machine to drag cotton pads containing remover over a dry film of nail polish. A densitometer was used to measure the opacity of the film before and after removal.

More specifically, the method involved glass microscope slides which were covered with a six mil (0.006 inches) wet film of nail polish and dried for three days. Ten slides were prepared for each product.

Round pads of cotton, 1 cm in diameter, were soaked with 100 μl of remover and placed into a holder on the Payoff Machine. The pad was dragged back and forth over the polish. A densitometer measured the opacity of the polish before and after removal.

The ratio of the opacity of the nail polish on the slide after and before application of the remover was calculated and transformed to the amount of polish removed. The results are listed in the accompanying Table I.

TABLE I

| TEST NO. | PRODUCT | POLISH REMOVED, % |
|---|---|---|
| 1 | 100% Acetone | 44.2 ± 2.9 |
| 2 | 85% Acetone 15% Water | 28.7 ± 2.7 |
| 3 | 75% Acetone 25% Water | 21.0 ± 1.5 |
| 4 | 75% Acetone 10.5% Propylene Carbonate 14.5% Water | 35.4 ± 2.2 |
| 5 | 75% Acetone 10.5% Estasol DBE 14.5% Water | 36.7 ± 1.9 |
| 6 | 75% Acetone 7% Propylene Carbonate 6.5% Estasol DBE 11.5% Water | 38.5 ± 1.1 |
| 7 | 75% Acetone 6.5% Propylene Carbonate 6.5% PPG-10 Butanediol 12% Water | 24.2 ± 2.6 |
| 8 | 75% Acetone 6.5% Propylene Carbonate 6.5% Butyl Carbitol Acetate 12% Water | 32.1 ± 2.1 |
| 9 | 75% Acetone 6.5% Propylene Carbonate 6.5% Alkyl Lactate 12% Water | 28.7 ± 1.7 |
| 10 | 75% Acetone 6.5% Propylene Carbonate 6.5% Tripropylene Monomethyl Ether 12% Water | 29.6 ± 2.0 |
| 11 | 75% Acetone 6.5% Propylene Carbonate 6.5% Propoxylated Butanol 12% Water | 25.9 ± 1.9 |
| 12 | 75% Acetone 6.5% Propylene Carbonate 6.5% Dipropylene Glycol n-Butyl Ether 12% Water | 26.3 ± 2.2 |
| 13 | 75% Acetone 6.5% Propylene Carbonate 6.5% Tripropylene Glycol n-Butyl Ether 12% Water | 31.1 ± 1.5 |
| 14 | 75% Acetone 6.5% Propylene Carbonate 6.5% Dipropylene Glycol Monomethyl Ether Acetate 12% Water | 26.6 ± 2.9 |
| 15 | 75% Acetone 25% Propylene Carbonate | 37.0 ± 2.7 |
| 16 | 75% Acetone 25% Estasol DBE | 36.2 ± 3.1 |
| 17 | 75% Acetone 12.5% Propylene Carbonate 12.5% Estasol DBE | 28.0 ± 2.1 |
| 18 | 75% Acetone 12.5% Propylene Carbonate 12.5% Water | 32.8 ± 2.3 |

Based on the results listed in the Table I, best performance was achieved by a combination of acetone, propylene carbonate, water and Estasol DBE. See Test No. 6. The presence of water in the acetone, propylene carbonate and Estasol DBE formulas increased lacquer removal efficacy from 28.0% up to 38.5%, while actually decreasing the volatile solvent from 100% down to 88.5%. Compare Test No. 6 with No. 17. The efficacy of water, the classic hydrophile, was thus unexpectedly effective in increasing solubilization of a hydrophobic lacquer.

EXAMPLE 2

A series of experiments were conducted to evaluate the effects of different levels of acetone, water and diester. Test procedures were identical to that described under Example 1. Results of these experiments are outlined in Table II.

TABLE II

| % WATER | DIESTER BLEND* % | DIESTER BLEND* Ratio | % POLISH REMOVED |
|---|---|---|---|
| \multicolumn{4}{c}{75% ACETONE} | | | |
| 2.3 | 22.7 | 1/10 | 30 |
| 5 | 20 | 1/4 | 33 |
| 8.3 | 16.7 | 1/2 | 35 |
| 12.5 | 12.5 | 1/1 | 34 |
| 16.7 | 8.3 | 2/1 | 25 |
| 18.25 | 6.25 | 3/1 | 21 |
| 20 | 5 | 4/1 | 16 |
| 22.7 | 2.3 | 10/1 | 15 |
| \multicolumn{4}{c}{80% ACETONE} | | | |
| 1.8 | 18.2 | 1/10 | 31.5 |
| 4 | 16 | 1/4 | 34 |
| 5 | 15 | 1/3 | 35 |
| 6.7 | 13.3 | 1/2 | 38 |
| 10 | 10 | 1/1 | 41 |
| 13.3 | 6.7 | 2/1 | 32 |
| 16 | 4 | 4/1 | 28 |
| 18.2 | 1.8 | 10/1 | 26 |
| \multicolumn{4}{c}{85% ACETONE} | | | |
| 1.4 | 13.6 | 1/10 | 27 |
| 3 | 12 | 1/4 | 29 |
| 5 | 10 | 1/2 | 29 |
| 7.5 | 7.5 | 1/1 | 31 |
| 10 | 5 | 2/1 | 33 |
| 11.25 | 3.75 | 3/1 | 31 |
| 12 | 3 | 4/1 | 30 |
| 13.6 | 1.4 | 10/1 | 29 |

*Mixture of 1:1 Estasol DBE with propylene carbonate.

The data according to Table II indicates that the formulas have an ability to remove nail polish which does not decrease as the amount of water is increased. Rather, there is an optimum amount of acetone, diester and water, which is maximized around an equal weight amount of water and diester blend. Of interest is that the amount of acetone does not seem to be as important as the amount of diester blend. Thus, the 85% acetone formulations do not do as well as the 75% acetone ones, the latter containing proportionately more of the diester blend.

The foregoing description and Examples illustrate selected embodiments of the present invention and in light thereof various modifications will be suggested to one skilled in the art, all of which are in the spirit and purview of this invention.

What is claimed is:

1. A polish-lacquer removing composition consisting essentially of:
   (i) from about 60 to about by 80% by weight of a volatile organic solvent selected from the group consisting of acetone, ethyl acetate and combinations thereof;
   (ii) from about 3 to about 20% by weight of a $C_4$-$C_{30}$ diester exhibiting a vapor pressure of less than 0.1 mm at 20° C.;
   (iii) from about 5 to about 20% by weight of water;
   (iv) optionally from 0 to about 20% by weight of propylene carbonate;
   (v) optionally from 0 to about 20% by weight of a humectant; and
   (vi) optionally from 0 to about 10% by weight of an emollient.

2. A composition according to claim 1 wherein the diester has the formula:

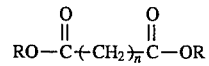

wherein R is a radical selected from the group consisting of $C_1$-$C_6$ alkyl and phenyl radicals; and n is an integer from 1 to 10.

3. A composition according to claim 2 wherein the diester is selected from the group consisting of dimethyl succinate, dimethyl glutarate, dimethyl adipate and combinations thereof.

4. A composition according to claim 1 wherein the diester and propylene carbonate are present in a respective weight ratio from about 5:1 to about 1:5.

5. A composition according to claim 1 wherein the volatile organic solvent is present in an amount from about 60 to about 75% by weight.

6. A method for removing polish-lacquer from fingernails comprising applying to the fingernails a composition consisting essentially of:
   (i) from about 60 to about 80% by weight of a volatile organic solvent selected from the group consisting of acetone, ethyl acetate and combinations thereof;
   (ii) from about 3 to about 20% by weight of a $C_4$-$C_{30}$ diester exhibiting a vapor pressure of less than 0.1 mm at 20° C.;
   (iii) from about 5 to about 20% by weight of water;
   (iv) optionally from 0 to about 20% by weight of propylene carbonate;
   (v) optionally from 0 to about 20% by weight of a humectant; and
   (vi) optionally from 0 to about 10% by weight of an emollient.

7. A method according to claim 6 wherein the diester has the formula:

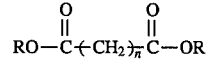

wherein R is a radical selected from the group consisting of $C_1$-$C_6$ alkyl and phenyl radicals; and n is an integer from 1 to 10.

8. A method according to claim 7 wherein the diester is selected from the group consisting of dimethyl succinate, dimethyl glutarate, dimethyl adipate and combinations thereof.

9. A method according to claim 6 wherein the diester and propylene carbonate are present in a respective weight ratio from about 5:1 to about 1:5.

* * * * *

UNITED STATES PATENT AND TRADEMARK OFFICE
CERTIFICATE OF CORRECTION

PATENT NO. : 5,486,305
DATED : January 23, 1996
INVENTOR(S) : Faryniarz et al.

It is certified that error appears in the above-indentified patent and that said Letters Patent is hereby corrected as shown below:

On the title page item [73],
Change the Assignee from "Chesebrough-Pond's USA Co.," to -- Chesebrough-Pond's USA Co., Division of Conopco, Inc. --

Signed and Sealed this

Twenty-eighth Day of May, 1996

*Attest:*

BRUCE LEHMAN

*Attesting Officer*     *Commissioner of Patents and Trademarks*